United States Patent [19]

Hertman et al.

[11] 4,169,886

[45] Oct. 2, 1979

[54] FOWL CHOLERA VACCINE AND ITS PREPARATION

[76] Inventors: Israel Hertman, 14 Biltmore St., Tel-Aviv; Ammon Michael, 50 Shaldag St., Hofit; Jacob Markenson, 23 Bar Kochba St., Tel-Aviv, all of Israel

[21] Appl. No.: 935,638

[22] Filed: Aug. 21, 1978

[30] Foreign Application Priority Data

Aug. 24, 1977 [IL] Israel ................................. 52815

[51] Int. Cl.$^2$ ............................................. A61K 39/02
[52] U.S. Cl. ...................................................... 424/92
[58] Field of Search ........................................ 424/92

[56] References Cited

PUBLICATIONS

Heddleston et al., Poultry Science, 54 (1): 217-221, Jan. 1975, "Fowl Cholera: Immunologic and Serologic Response in Turkeys to Live *Pasteurella multocida* Vaccine Administered in the Drinking Water".
Sulong et al., Veterinary Microbiology, 1 (1): 3-14 (1976), "Studies on Pasteurella multocida IV, Immunoflurescence Detection of the Organisms in Spleen and Lungs of Turkeys Vaccinated with Live Oral Vaccines".
Coates et al., Poultry Science, 56 (1): 273-276 (1977), "The Response of Turkeys to Varying Doses of Live Oral *Pasteurella multocida* Vaccine".
Bierer, Poultry Science 56 (1): 327-330 (1977), "An Evaluation of the Effect of Various Concentrations of the Clemson University *Pasteurella multocida* Drinking Water Vaccine on the Immune Response Against Fowl Cholera Disease in Turkeys".

*Primary Examiner*—Shep K. Rose
*Attorney, Agent, or Firm*—Fleit & Jacobson

[57] ABSTRACT

The present invention relates to a live vaccine against *Pasteurella multocida*, for application of poultry by injection, per os or as aerosol, containing an attenuated non-virulent genetically stable strain of *Pasteurella multocida*, to a process for producing an attenuated genetically stable non-virulent strain of *Pasteurella multocida*, which comprises cultivating a virulent field strain, selecting after 18 hours at 37° C. colonies of uniform size, of about 4 to 5 mm diameter, suspending these in a pH 5.5 buffer, subjecting same to a mutagen at a concentration causing a mortality of 90-99% after 30 minutes at 37° C., centrifuging the microorganisms, washing same, plating same and selecting colonies of not more than 2.5 to 3 mm diameter after 18 hours at 37° C., purifying by reisolation of single colonies, testing for antigenic specificity and virulence, and selecting avirulent genetically stable immunologically effective mutants for use in vaccines, and to a process for the vaccination of poultry which comprises applying such a vaccine by injection, per os or as aerosol.

4 Claims, No Drawings

FOWL CHOLERA VACCINE AND ITS PREPARATION

FIELD OF THE INVENTION

The present invention relates to a live vaccine against *Pasteurella multocida*, comprising a novel, avirulent strain of the above microorganism. The invention further relates to a process for the production of mutants of field strains of the above microorganism which are avirulent, suitable for producing vaccines against Fowl Cholera, and which are stabilized in their genetic constitution to remain avirulent. The invention further relates to a novel attenuated strain, designate as M-3-G, and which has been deposited as ATCC No. 31416.

BACKGROUND OF THE INVENTION

One of the common fowl diseases is Fowl Cholera, caused by *Pasteurella multocida*. This disease is also known as Pateurellosis. The disease is prevalent amongst turkeys and chickens and the mortality is quite high and thus economic losses are sever. The disease is contagious and premises remain infected over prolonged periods of time. Especially susceptible are turkeys and male chickens which are used for breeding purposes.

STATE OF THE PRIOR ART

The first attenuated vaccine of this type was developed by Pasteur: Compt. Rend. Acad. Sci. 91, 673 (1880) but this had the drawback that the bacteria reverted to their virulence.

A naturally occurring strain of low virulence, the Clemson University (CU) strain was reported in Poultry Science 47 1162 (1968). This was found in nature, it is of comparatively low virulence, it is stable and it is effective in the immunization of turkeys. It is of lesser effectivity when used on chickens, and especially when applied orally. Individual injections are effective, but this constitutes a serious drawback. Furthermore, a rate of mortality of up to 2%, and even higher is observed if the birds harbour other microorganisms, such as *Mycoplasma gallisepticum*, see Poultry International, April 1975, p' 12.

Over the years commercial inactivated (killed) vaccines or bacterins have been used for the immunization of poultry against fowl cholera. The disadvantages are that such vaccines confer immunity only against the specific strain of the vaccine. Many strains exist and new ones appear occasionally and the immunization is not effective against these. Such vaccines must be applied by individual injection; adjuvants must be used and these cause often "knots" at the site of the injection. By 2 or 3 injections a duration of immunity of only about 8 to b 10 weeks is attained. Many of the drawbacks of the conventional vaccines are eliminated by the novel vaccine according to the present invention.

SUMMARY OF THE INVENTION

The present invention relates to a novel live vaccine for the vaccination of poultry against *Pasteurella multocida*, by injection, per os, or by aerosol, which comprises an attentuated avirulent, stable strain of this microorganism. The invention further relates to a process for converting field strains of this microorganism to attenuated, stable non-virulent strains which can be used as active ingredient in vaccines. The invention further relates to such attenuated strains, and especially to a strain designated as M-3-G, deposited as ATCC No. 31416, and to vaccines containing this attenuated non-virulent, genetically stable strain.

The novel attenuated strain according to the present invention and vaccine prepared from such strains have a number of important advantages, such as: The attenuated strain are completely avirulent to turkeys and chickens; they are genetically stable and do not revert to the original virulence, they do not cause any mortality when applied to birds harbouring Mycoplasma spp., the immunity lasts appreciably longer and the immunity is effective against all strains of *Pasteurella multocida*, and even against new strains which appear from time to time. The fact that the immunity is against homologous as well as heterologous strains is of special importance.

The M-3-G strain is of Serotype 1 (Heddleston) and it is the result of a controlled and reproducible mutation. It differs in a number of significant parameters from the field strain FS-3, type X-73, also deposited with the ATCC, and obtainable from ATCC, as will be set out in detail in the following. Amongst the differences there may be mentioned different colony size, absence of hyaluronic acid from its capsule and prolonged generation time. Repeated passage via the intravenous route through turkeys demonstrated the stability of the novel strain as regards all the properties noted. The strain is completely avirulent and doses as high as $10^{11}$ microorganisms per turkey, applied by various routes, caused no adverse effects.

K. L. Heddleston described 16 serotypes of *P. multocida*, numbered 1 to 16, and isolated from chickens, turkeys, buffalo, wild birds etc. The process according to the present invention, based on the use of a mutagenic substance, is applicable to the different serotypes and it is possible to obtain attenuated avirulent strains, and vaccines containing same, by the process of the invention. The novel strains are avirulent, genetically stable and confer immunity which is long lasting. Application per os or by aerosol is convenient and suited for mass immunization.

The attenuated M-3-G strain, deposited as ATCC No. 31416 was developed from a virulent field strain, identified as FS-3, of Serotype 1 by the Heddleston classification, performed by the test of Little et a., Am. J. Vet. Res. 4, 110 (1943). This is also designated as X-73 and available from ATCC No. 11039. Contrasted with conventional vaccines which result in a mortality of about 1 to 3% if a hidden disease is present, the novel vaccines according to the present invention are practically devoid of side-effects. The effectivity of the vaccine is a high one (80 to 100%). The novel vaccines are preferably applied orally (preferably in drinking water) or by aerosol. Oral dosages are about $10^8$ to $10^{11}$ attenuated microorganisms and preferably about $10^{10}$ per bird. The vaccine can be lyophilized and stored over prolonged periods of time. The lyophilized substance contains about 2 doses per milligram of dry material and this is reconstituted prior to use by suitable dilution.

The process for the production of attenuated genetically stable mutants, which are avirulent and which can be used for the effective vaccination against Fowl Cholera is described in detail in the experimental part, and it comprises the following essential steps: The virulent field strain is grown on a suitable culture medium and after 18 hours at 37° C. uniform colonies of about 4–5 mm diameter are selected. The microorganisms are suspended in a buffer of about pH 5.5 and a suitable mutagen is added in a concentration resulting in a survival rate of about 1 to 2% after 30 minutes at 37° C. Especially good results were obtained with N-methyl-N-nitroso N-nitro guanidine (NTG). Other mutagenic substances such as methyl methane sulfonate (MMS), ethyl methane sulfonate (EMS), 5-bromo uracyl, 2-amino purine and hydroxylamine can also be used. After centrifugation and washing the microorganisms are suspended in a pH 7.2 buffer, diluted and plated at a concentration of about 100/plate. About 95-99% of the colonies are of conventional size and type, 1 to 5% are mutants. Colonies which have a diameter of less than about 2.5 to 3 mm after 18 hours at 37° C. are chosen, purified by reisolation of single colonies, not exceeding this size, tested for antigenic specificity, tested for virulence and the avirulent strains are cultivated and tested for genetic stability by repeated passage through birds. The strains having the best immunogenic properties were selected. The strain selected as best one is designated as M-3-G and as ATCC 31416. This has a generation time substantially different from that of the parent X-73 strain. The generation time is 27 minutes at 37° C. and 24 minutes at 41° C. for the parent strain, and 30 minutes at 37° C. and 39 minutes at 41° C. for ATCC 31416. Body temperature of birds is about 41° C. This mutant has no hyaloronic acid in its capsule.

The virulence of the mutant is substantially decreased. While 8.8 organisms of the parent strain kill 5 out of 5 mice injected i.p. within 2 days and 88 microorganisms kill 5 out of 5 mice within 24 hours, M-3-G did not cause the death of any of 10 mice injected i.p. with $10^7$ microorganisms.

As pointed out above, the novel vaccine is devoid of side-effects and immunity resulting from 2-3 consecutive oral application in drinking water lasts for about 10 weeks or more.

DESCRIPTION OF THE PREFERRED EMBODIMENT

The invention is illustrated with reference to the following Example and experimental results, which are by way of illustration only and which are to be construed in a non-limitative manner.

PRODUCTION OF VACCINE a. Strains.

Five field strains representing the *Pateurella multocida* serotypes, Haddleston et al, 1972, Avian Dis. 16, 703, were grown to a concentration of $10^8$ bacteria/ml at 37° C. in 5 ml of LB-Broth (10 g Bacto trypton, 5 g Yeast extract, 10 g NaCl, 1 g glucose, in 1000 ml distilled water). The cultures were diluted in a diluent (10 g Bacto trypton, 5 g NaCl in 1000 ml water) to a concentration of about 1000 bacteria/ml and 0.1 ml samples were plated on LB agar (LB Broth supplemented with 10 g/l agar, Difco and 200 mg/l of hemin). Colonies were observed after 18 hours at 37° C. All the media were maintained at pH 7.2.

Strain F-S-3 (serotype 1) equivalent to strain X-73, ATCC 11039, gave colonies of a substantially uniform size of 4 to 5 mm diameter. FS-3 gave the best reproducibility of viability counts. Strain FS-3 and the other strains were examined as regards formation of colonies after lyophilization. It could be lyophilized without loss in colony forming units exceeding 90%. This strain was selected for mutagenesis.

b. Mutagenesis.

FS-3 bacteria from frozen stock cultures were thawed, inoculated into LB Broth (1 ml stock culture to 10 ml LB Broth) and cultivated at 37° C. in 50 ml Erlenmayer flasks with reciprocal shaking. Cultures were diluted after 18 hours 1 to 60 into 5 flasks each containing 10 ml of fresh LB-Broth and grown to mid-log phase (about $10^8$ bacteria per ml). The cultures were harvested by centrifugation at 10,000 rpm/10 minutes. The sediment was washed and resuspended in 10 ml of citrate buffer of pH 5.5.

N-methyl-N-nitro-N-nitroso guanidine (NTG) was added to the suspensions of the bacteria to the following final concentrations: 25, 50, 100 and 200 μg/ml. The bacterial suspensions containing different concentrations of NTG were incubated in a water-bath during 30 minutes at 37° C. (without aeration). After this incubation period each culture was centrifuged at 10,000 rpm during 10 minutes and the sediment was washed twice with phosphate buffer of pH 7.2. The washed sediment containing the treated bacteria was resuspended in 10 ml of fresh LB Broth and incubated in flasks for 18 hours at 37° C. with aeration and reciprocal shaking. Viability of bacteria was determined by plating on LB agar immediately after incubation with NTG before centrifugation. At the above concentrations of NTG the mortality was 15, 40, 90 and 99 percent respectively. The calibration of NTG was carried out with each culture of *P. Multocida* treated with the mutagen. Only cultures with 90-99% mortality after exposure to NTG were taken for further selection procedures.

c. Isolation of Attentuated Mutants.

500 Bacterial clones surviving NTG treatment were picked up by sterile toothpicks, purified genetically by twice streaking on agar plate surfaces and reisolation of single colonies. The purified clones were grown overnight at 37° C. and colonies of less than 3 mm diameter were selected. These were diluted 1/50 in LB Broth, cultivated 18 hours with aeration at 37° C. and tested for virulence by injecting at least 4 mice introperitoneally with $10^6$ bacteria. The parental strain FS-3 injected at this concentration caused 100% death after 10 to 18 hours. By this method 11 strains were isolated which were avirulent to mice. These were further tested in turkeys 5 weeks old. The strains were designated 1T, 5T, 6T, 7T, 8T, 9T, M3, M4, ITG, M3G, M4G. Six of the 11 strains were found to be attenuated (avirulent) in turkeys. The selected strains were tested for immunogenic properties and M3G was found to be the best one. This strain has the properties set out in the following Table.

CHARACTERISTICS OF PASTEURELLA MULTOCIDA M-3-G

1. Heddleston Serotype 1, identified by agar precipitation and rapid agglutination tests.
2. No hyaluronic capsule present; agglutinable with specific antiserum (anti-) without pretreatment with hyalusonidase.
3. Generation time about 30 minutes at 37° C. in LB-Broth end 39′ at 41° C.

| 4. | Antibiotic resistance pattern: | | |
|---|---|---|---|
| | Streptomycin | 5 μg | non-sensitive |
| | Tetracycline | 10 μg | sensitive |

-continued

| 4. Antibiotic resistance pattern: | | |
|---|---|---|
| Penicillin | 5 μ-units | fairly sensitive |
| Cephalotin | 30 μg | very sensitive |
| Erythromycin | 5 μg | resistant |
| Chloromycetin | 10 μg | very sensitive |
| Novobiocin | 10 μg | very sensitive |
| Kanamycin | 10 μg | very sensitive |
| Methicillin | 10 μg | very sensitive |

The resistance pattern was determined by disk-tests (Difco) on LB agar plates and by measurement of the inhibition zones after 18 to 24 hours.

The parental FS-3 is sensitive to steptomycin and erythromycin and to the other antibiotics.

5. Avirulent to mice (i.p. $10^6$ bacteria), turkeys (i.p. $10^8$ bacteria).

6. No reversion to virulence after passage through turkeys: $10^8$ bacteria were injected i.v., the animals were sacrificed 20 to 30 hours later and bacteria were isolated aseptically from the liver. Maximum number of bacteria per liver: 100 to 1000.

This was repeated 10 times and the final crop of bacteria, after the tenth bird-to-bird passage was reisolated and susceptible turkeys were inocculated with $10^{10}$ bacteria per bird. No harm was done to the birds and it is clear that the bacteria did not revert to their virulence.

The bacteria retained also their other characteristics: such as absence of hyaluronic acid in the capsule, formation of microcolonies of less than 3 mm diameter after 18 hours at 37° C. and the diminished generation time (about 39 minutes at 41° C.).

7. Survives freezing in 8% glycerol in broth and also lyophilization.

8. Survives at least 2 hours in drinking water supplemented with 0.25% milk powder at 25° C.

PRODUCTION OF VACCINE

Strain M-3-G was inoculated into 500 ml tryptose broth and incubated overnight at 37° C. The obtained culture was checked for purity by microscopic examination of gram stained smears and for ability to agglutinate without pretreatment with hyaluronidase. It was plated out and checked biochemically and serologically. The thus obtained culture was used as inoculum and it was aseptically transferred to a 40 liter fermentor which was charged with presterilized culture medium comprising tryptose, yeast extract, peptone, dextrose and buffering salts. The pH was controlled during the cultivation process. The culture medium was periodically monitored for growth of M-3-G by photometric density measurements of samples withdrawn. When the growth reached its peak, the suspension was transferred to precooled vessels and the organisms were concentrated by centrifugation. The concentrated produce was resuspended in a suitable medium, such as milk carbohydrates or casein hydrolysate and dispensed into ampuled and vials and frozen.

The frozen vaccine was lyophilized and the resulting dry vaccine was tested for purity and culture characteristics, stability under refrigeration (+4° C.) and this vaccine was used for tests with birds, the results of which are given hereinafter. The results obtained prove that the vaccine is substantially superior to the killed-organism type vaccine used hitherto and that it can be applied by considerably more convenient means.

TEST OF VACCINE FOR ITS EFFICACY

Susceptible turkeys were repeatedly inoculated with strain M-3-G. This was effected via various routes: in one experiment turkeys were injected 3 times intramuscularly in doses of $7.10^7$ to $4.10^8$. The inoculated turkeys and uninoculated controls were challenged by injection with virulent *Pasteurella multocida*, using the parent strain FS-3 and heterologous strains, which were serologically different. The results are given in following Table 1.

TABLE 1

| Challenge Strain | Death after Challenge | |
|---|---|---|
| dosage applied: | Controls (unvaccinated) | Vaccinated M-3-G |
| Homologous Challenge | 16 out of 19 | 0/18 |
| $1.6 \times 10^3$/bird | 84.2 % | 0 % |
| Heterologous challenge | 16 out of 17 | 3/18 |
| $2.4 \times 10^3$/bird | 94.1 % | 16.6 % |

In another experiment M-3-G was tested by application of vaccine to turkeys per os. A quantity of $10^{10}$ bacteria in 100 ml drinking water was applied per bird. Application was 3 times with weekly intervals. 2 weeks after the last dose the turkeys were challenged i.m. and by the respiratory route using the palatine cleft to rub in the challenge strain, at $10^8$ cfu/ml simulating infection in the field. Results are given in Table 2.

Immunization can also be applied by inhalation of an aerosol. A quantity of $10^{10}$ bacteria in 50 ml water was aerosolozed within 10 minutes and birds were exposed to this cloud.

TABLE 2

| | CHALLENGE RESULTS | | | |
|---|---|---|---|---|
| Bird Group | Challenge with homologous strain | | Challenge with heterologous Strain | |
| & Treatment | Challenge intramuscularly | Challenge via Respiratory Tract | Challenge intramuscularly | Challenge via Respiratory Tract |
| Controls (unvaccinated) | 13/18* 72.2% | 20/20 (100%) | 15/18 (83.3%) | 9/15 (60%) |
| M-3-G Vaccinated Intramuscularly | 4/20 (11.8%) | NOT DONE | 8/17 (57.1%) | NOT DONE |
| M-3-G Vaccinated via Drinking Water | 2/30 6.66% | 4/24 (16.6%) | 2/30 (6.66%) | 0/18 (0%) |

*13/18 = 13 dead out of 18 challenged test animals.
The results of efficacy tests further improved in later experiments when the minimum challenge dose was determined.

What is claimed is:

1. A live vaccine aginst Pasteurella multocida, for application to poultry by injection, per os or as aerosol, containing an attenuated non-virulent genetically stable strain of Pasteurella multocida which is M-3-G., ATCC No. 31416.

2. A vaccine according to claim 1 in unit dosage form, containing about $10^8$ to $10^{11}$ bacteria per bird dosage.

3. A method for the vaccination of poultry which comprises applying the vaccine of claim 1 in an immunologically effective amount, by injection, per os, or as aerosol.

4. A method according to claim 3, wherein the dose per bird is $10^8$ to $10^{11}$ bacteria.